United States Patent [19]
Rozmus et al.

[11] Patent Number: 6,064,752
[45] Date of Patent: May 16, 2000

[54] METHOD AND APPARATUS FOR POSITIONING SUBJECTS BEFORE A SINGLE CAMERA

[75] Inventors: J. Michael Rozmus, Medford; Michael Negin, Tabernacle; Guy Dela Rosa, Trenton; Anthony O'Brien, Marlton, all of N.J.

[73] Assignee: Sensar, Inc., Moorestown, N.J.

[21] Appl. No.: 08/964,452

[22] Filed: Nov. 4, 1997

[51] Int. Cl.[7] .................................................. G06K 9/00
[52] U.S. Cl. ........................ 382/117; 348/77; 351/206; 351/219
[58] Field of Search ........................ 382/100, 115–118; 340/439, 575, 576; 351/200, 205, 208–211, 213, 219, 221, 222, 206, 207; 348/77, 78, 131, 132, 306, 308

[56] References Cited

U.S. PATENT DOCUMENTS

| | | | |
|---|---|---|---|
| 4,208,105 | 6/1980 | Hadwiger | 350/306 |
| 4,288,819 | 9/1981 | Williams | 358/226 |
| 4,620,318 | 10/1986 | Hill | 382/2 |
| 4,641,349 | 2/1987 | Flom et al. | 382/2 |
| 4,753,527 | 6/1988 | Ishihara | 351/244 |
| 4,772,095 | 9/1988 | Spencer | 350/172 |
| 5,016,282 | 5/1991 | Tomono et al. | 382/2 |
| 5,291,560 | 3/1994 | Daugman | 382/2 |
| 5,359,669 | 10/1994 | Shanley et al. | 351/205 |
| 5,608,489 | 3/1997 | Ozaki | 351/210 |
| 5,717,512 | 2/1998 | Chmielewski, Jr. et al. | 359/210 |
| 5,801,763 | 9/1998 | Suzuki | 348/77 |

*Primary Examiner*—Bhavesh Mehta
*Attorney, Agent, or Firm*—Buchanan Ingersoll, P.C.

[57] ABSTRACT

A system and method of positioning a head of a subject to be photographed by a single camera uses a mirror and at least one collimated light beam. The single camera is positioned so that there is a selected specific location in space within a field of view of the camera at which the head or eye of the subject is desired to be positioned. A light source directs a collimated light beam or light sheet so that the light beam or light sheet intersects a line running from the mirror through the selected specific location in space and can be seen by an eye at the selected specific location in space that is looking at the mirror. The user is told to position his head across from the mirror and move his head until he sees the collimated light beam or light sheet and his eye in the mirror. When the subject is so positioned the single camera can take an image of the eye from which the subject can be identified. If desired a second mirror can be used in place of the light source.

72 Claims, 3 Drawing Sheets

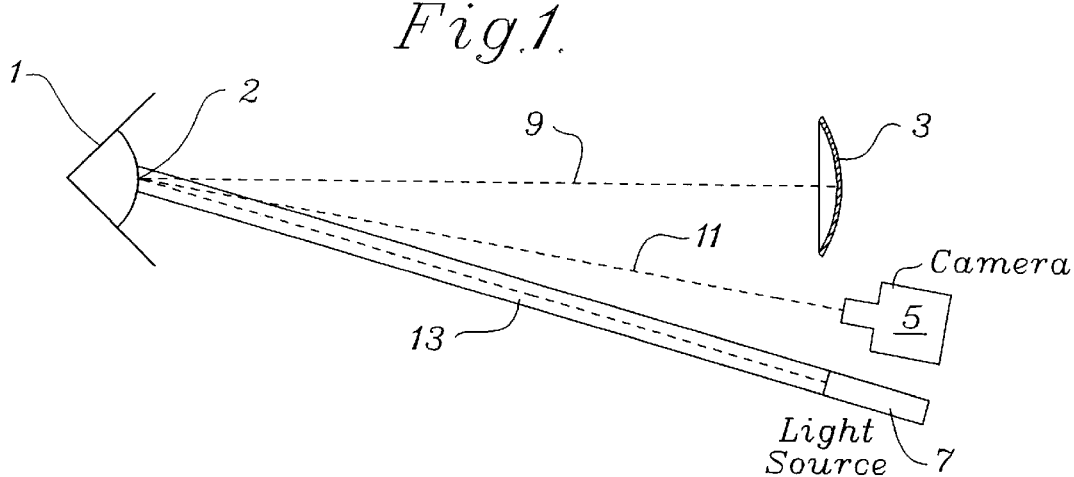
*Fig.1.*
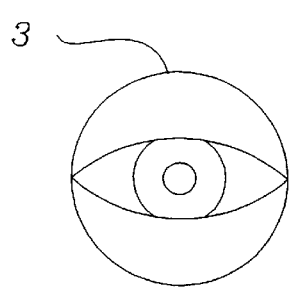   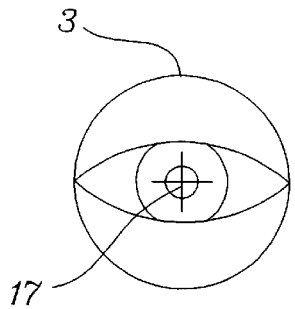   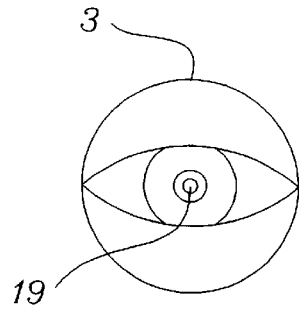
*Fig.2.*   *Fig.3.*   *Fig.4.*
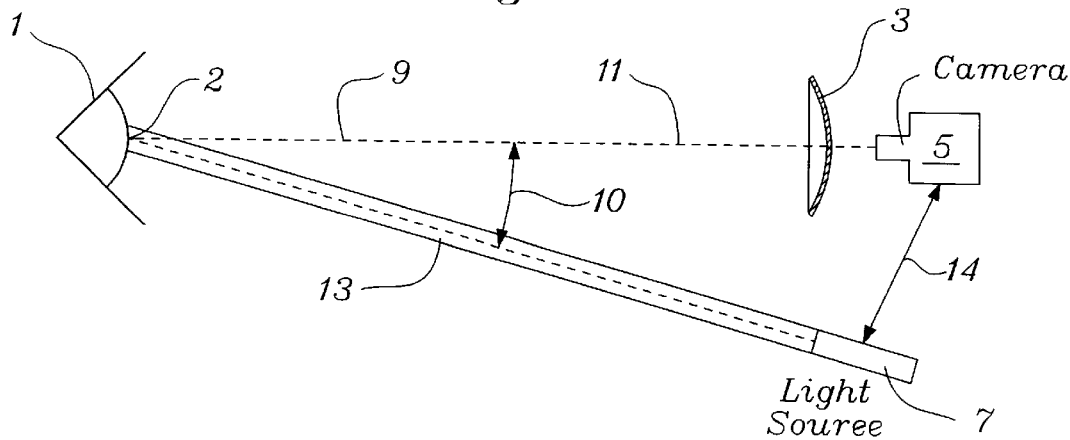
*Fig.5.*

METHOD AND APPARATUS FOR POSITIONING SUBJECTS BEFORE A SINGLE CAMERA

FIELD OF THE INVENTION

The invention relates to identifying individuals from facial images, and more particularly from images of the eye.

BACKGROUND OF THE INVENTION

There are several methods known as biometrics for recognizing or identifying an individual. Some of these methods involve imaging of the face or eye and analyzing the facial features, retinal vascular patterns of the eye or patterns in the iris of the eye. A technique for iris recognition is described in U.S. Pat. No. 4,641,349 to Flom et al. and in U.S. Pat. No. 5,291,560 to Daugman. The systems described in these references require the person being identified to hold at least one of their eyes in a fixed position with respect to an imaging camera that takes a picture of the eye. In a commercial embodiment produced by the owner of these patents, the person is required to press his eye against an eye piece. This assures that the eye is at a correct distance from a camera to create a useful image. While this procedure is satisfactory for some applications, it is not satisfactory for quick transactional activities such as using an automated teller machine or providing unobtrusive access to a secured area or a secured system, such as a computer system.

In U.S. pat. application Ser. No. 08/648,324 there is disclosed an automated teller machine which relies upon three cameras to identify the subject of an automated teller machine. The first two cameras are wide field of view cameras which find the subject's head and locate the eye position in the image. A three-dimensional position in space for the eye is calculated from the images. From that information a narrow field of view camera is directed to that position. The narrow field of view camera then takes an image of the eye from which identification can be made. Although such a system has been made to work quite well, the use of multiple cameras is expensive. Thus, there is a need for a single camera system which can acquire an image of the eye useful for identification of the individual. This system should be easy to use and minimally intrusive.

SUMMARY OF THE INVENTION

We provide a method of positioning the eye of a subject to be photographed by a single camera using a mirror in conjunction with a collimated light beam or a second mirror. First we position the single camera so that there is a specific location in space, where the camera is aimed and focused, at which the eye of the subject is desired to be positioned for a good image. When the subject looks at the image of his eye in the mirror, a line of sight is defined between the mirror and the eye of the subject. We further provide a collimated light source that directs a collimated light beam from a direction off of the line of sight in a manner so that the light beam intersects the line of sight at the specific location in space where the camera is aimed and focused. As an alternative to the light beam, we provide a second mirror in which the subject looks at the image of his eye establishing a second line of sight. We instruct the subject to position his eye in the center of the mirror, and move his head closer to or farther from the mirror until he sees the collimated light beam (or until he sees his image in the center of the second mirror). When the subject is so positioned the single camera can capture a good image from which the subject can be identified.

BRIEF DESCRIPTION OF THE FIGURES

FIG. 1 is a diagram showing a subject's eye in relation to the major elements of a first preferred embodiment of the new positioning device. These elements are a mirror, a camera, and a collimated light source.

FIGS. 2, 3, and 4 are diagrams which depict three different views of the subject's own eye in the mirror showing three ways of aligning the subject's eye along the required line-of-sight.

FIGS. 5, 6, and 7 are diagrams showing alternative arrangements of the major elements of the our positioning device comprising second, third, and fourth preferred embodiments.

DESCRIPTION OF THE PREFERRED EMBODIMENTS

Figure 6:
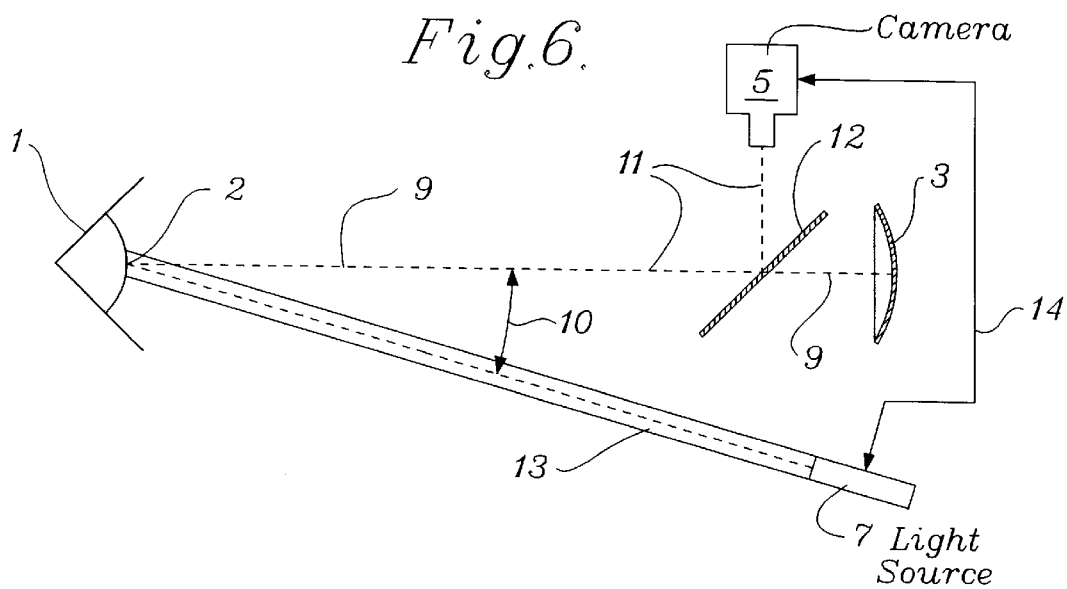

In FIG. 1, we show the major elements of a first preferred embodiment of the present invention. An eye 1 of a subject is looking into a mirror 3 to establish a line of sight 9. A collimated light source 7 generates a collimated light beam 13 in such a way that the light may only be seen by the subject at the unique location 2 where the light beam 13 intersects the line of sight 9. Typically point 2 will be a selected specific location in space. A camera 5 is aimed and focused at this unique location 2. Thus, the line of the optical axis 11 of the camera 5 will also pass through point 2 and the focal point of the camera 5 will be at point 2.

In a second preferred embodiment shown in FIG. 5, the line of sight 9 and the optical axis 11 of the camera 5 are made to coincide by placing the camera 5 behind the mirror 3. This requires that the mirror 3 be a cold mirror for infrared imaging or partially transparent for visible light imaging. (A cold mirror is one which reflects visible light but is essentially transparent to infrared radiation.)

The line of sight 9 and the optical axis 11 of the camera 5 partially coincide in a third preferred embodiment shown in FIG. 6. A flat mirror 12 is placed on the line of sight 9, at an angle of about 45 degrees to the line of sight 9, in front of the mirror 3 to deflect the optical axis 11 of the camera 5. The mirror 12 must be a hot mirror for visible light imaging, or the mirror 12 must allow infrared light to Pass for infrared imaging. (A hot mirror reflects infrared radiation but is essentially transparent to visible light.) If the mirror 12 is transparent to visible light, a reflection of light from the subject's eye 1 passes through mirror 12 onto mirror 3. That light is reflected back through the tilted mirror 12 to the subject. Thus, he will be able to see a reflection of his eye in the mirror 3.

In the second and third preferred embodiments illustrated in FIGS. 5 and 6 respectively, the focus of the camera 5 need not be fixed at a specific distance along the optical axis 11, as is assumed in the first preferred embodiment of FIG. 1. The manual focus mechanism of the camera 5 may be mechanically or electronically linked as indicated by double headed arrow 14 to the aiming of the collimated light source 7 in such a way that the angle 10 between the optical axis 11 of the camera 5 and the collimated light beam 13 is adjusted with the focus so that the collimated beam 13 intersects the optical axis 11 of the camera 5 at the distance where the camera 5 is focused. For this option, the subject does not move closer or farther from the positioning device until the collimated beam 13 is visible, but instead the subject adjusts the manual focus while remaining at a fixed distance from the positioning device until he can see the collimated light beam 13, indicating that the focus of the camera 5 is now adjusted to the location of his eye 1.

Figure 7:
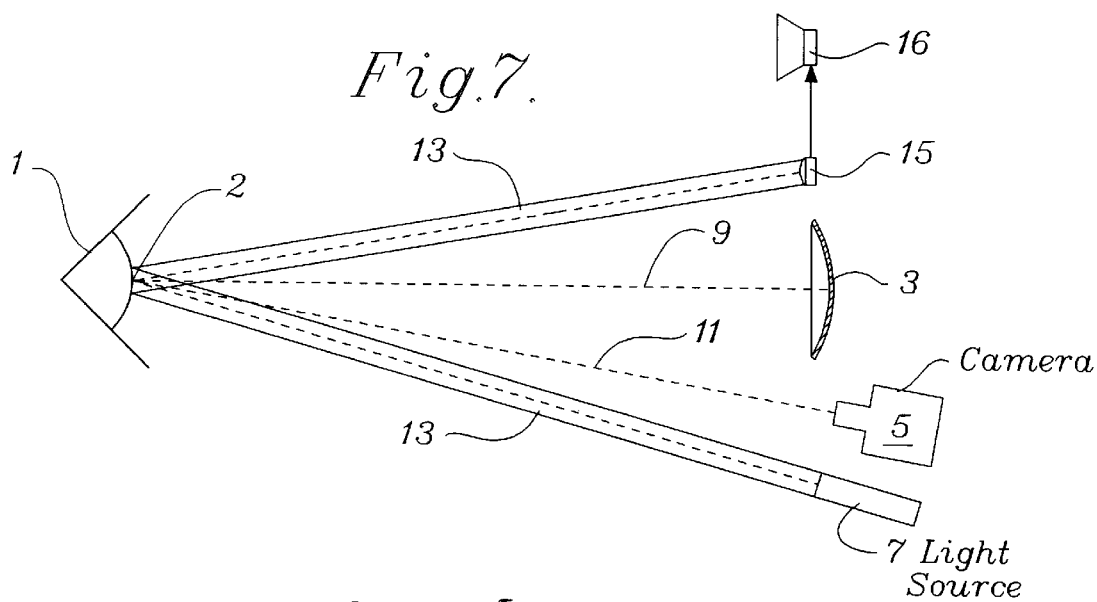

In FIG. 7, a fourth preferred embodiment is shown. This arrangement does not depend on the subject to detect the collimated light beam 13 by sight. Instead, the specular reflection of the beam 13 from the surface of the eye 1, or from eyeglasses if they are present, is detected by a photodetector 15. The only location on the line of sight 9 where the eye 1 can cause this reflection is where the collimated beam 13 intersects the line of sight 9, which is, by design, the unique location where the camera 5 is aimed and focused. When the photodetector 15 senses the specular reflection, this fact is indicated to the subject by an audible tone from a speaker 16, a luminous indicator 19 which may be in the mirror 3 as shown in FIG. 4, or other such means so that the subject will hold his eye 1 in the correct position. Alternatively, the presence of the specular reflection may be detected by image processing of the views seen by the camera 5. In this latter case, the photodetector 15 is not necessary. This fourth preferred embodiment, and all of the preferred embodiments described above, may be implemented using visible light or infrared radiation.

Figure 10:
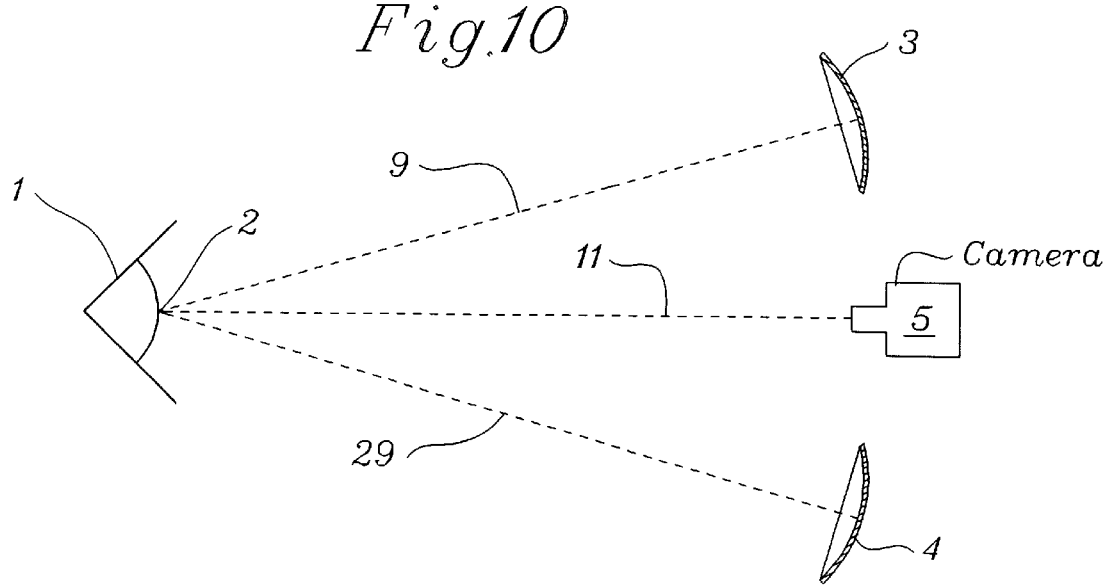
FIG. 10 is a diagram showing a fifth present preferred embodiment in which a second mirror is substituted for the collimated light.

A fifth preferred embodiment shown in FIG. 10 is the same as the first preferred embodiment of FIG. 1 except that the collimated light source 7 and the collimated light beam 13 are replaced by a second mirror 4 and a second line of sight 29. In this case, the subject is asked to move closer to or farther from his image in mirror 3 along the line of sight 9 until he sees his image in the mirror 4. (Of course, the use of the mirrors could be reversed.) The eye 1 of the subject is now at the desired location 2 at the intersection of line of sight 9 of mirror 3 and line of sight 29 of mirror 4 where the camera 5 is aimed and focused.

Similar substitution of a second mirror 4 for the light source 7 can also be made in the second and third preferred embodiments of FIGS. 5 and 6. As in the original second and third preferred embodiments, the focal point of the camera 5 would not need to be fixed at a specific distance along the optical axis 11 for the two-mirror variations. The manual focus mechanism of the camera 5 may be mechanically or electronically linked to the aiming of the second mirror 4 in the same manner as previously explained for the aiming of the collimated beam 13.

Various methods may be used to aid the subject in establishing the desired line of sight 9. The subject may be asked to simply place the image of his eye 1 in the center of the mirror 3 to see the view illustrated for a circular mirror 3 in FIG. 2. The subject might also be asked to center the image of his eye 1 on a target 17 inscribed on the mirror 3 to see the view shown in FIG. 3. As another alternative, the subject might be asked to center the image of his eye 1 on a small luminous indicator 19, such as a light emitting diode, mounted in the surface of the mirror 3 to see the view shown in FIG. 4. When the subject does any of these things his line of sight will be a segment of a line that passes from the mirror through the selected specific location in space. All of these methods apply equally well to the second mirror 4.

The front surface of the mirror 3 that is shown in FIGS. 2, 3, and 4 is circular; but this is not essential for the present invention. Other shapes would also be adequate. The view of the mirror 3 illustrated in FIGS. 1, 5, 6, and 7 shows the mirror to be curved. A concave mirror is used to give some magnification to the reflected image of the eye 1 to aid the subject in seeing the image when the distance from the eye 1 to the mirror 3 is relatively large. However, this is not essential for the present invention. At relatively small distances, a flat or even convex mirror would be adequate. All of these variations also apply to the second mirror 4.

The collimated light beam 13 may be formed by various well-known means such as a converging lens with a source at its focal point, a parabolic reflector with a source at its focal point, or an aperture at some distance away from a source. Even a source with a narrow cone-shaped pattern of emission may be an adequate approximate implementation and can for purposes of this invention be considered to be a collimated light beam source. Furthermore, a sheet of light in a well-defined plane may be used as a substitute for the collimated light beam 13 because the intersection of the line of sight 9 and a sheet of light is still a single unique location. Thus, one can consider the collimated light beam 13 shown in FIGS. 1, 5 and 6 as an edge view of a light sheet.

The cross-sectional shape of the collimated light beam is not critical to the present invention. It may be a circle, a rectangle, a cross, or any other small shape. Specific shapes may be more or less helpful to the detection of the specular reflection by image processing in the fourth preferred embodiment described above.

Figure 8:
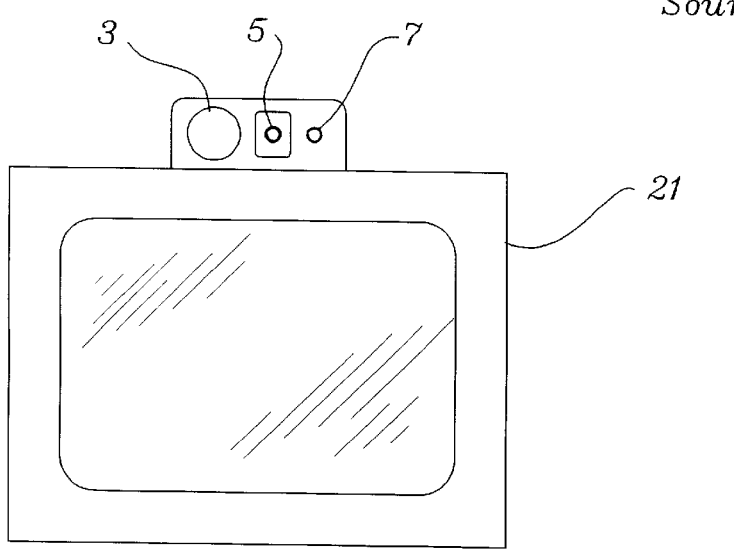
FIG. 8 is a subject's view of our positioning device, using the order of the arrangement of major elements shown in FIG. 1, mounted horizontally on the top of a video display.
Figure 9:
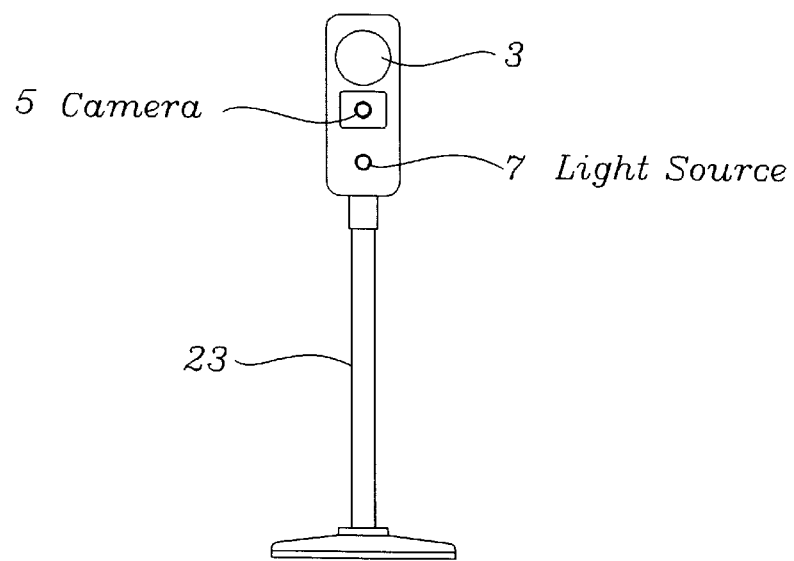
FIG. 9 is a subject's view of our positioning device, using the order of the arrangement of major elements shown in FIG. 1, mounted vertically on the top of a desktop stand.

The apparatus of the present invention may be mounted in various ways to maximize ease of use for the subject. For example, FIG. 9 shows the arrangement of the first embodiment mounted vertically on a desktop pedestal 23. In FIG. 8, the major elements of the system, the mirror 3, the camera 5, and the collimated light source 7, are in the same order but they are arranged horizontally and mounted on the top of a video display 21. The device might also be mounted on a keyboard, a door, a wall, or any other convenient location with major elements arranged horizontally or vertically. This is true of all the preferred embodiments described above. It is not even strictly necessary that the major elements of the present invention be in the same plane, so long as the line of sight 9 and the collimated light beam 13 (or second line of sight 29) intersect at the unique location 2 where the camera 5 is aimed and focused to get a good image of the eye 1 of a subject.

Although we have shown certain present preferred embodiments of our invention, it should be distinctly understood that the invention is not limited thereto, but may be variously embodied within the scope of the following claims.

We claim:

1. A method of positioning an eye of a subject to be photographed by a camera comprising the steps of:

a. selecting a specific location in space within a field of view of the camera at which an eye of the subject is desired to be positioned;

b. providing a mirror at a fixed distance from the selected specific location in space such that the subject can see a reflected image of his eye at a particular spot in the mirror only when his line of sight is a segment of a line that passes through the selected specific location in space;

c. directing a collimated light beam in a manner so that the light beam passes through the selected specific location in space; and d. instructing the subject to position his head so that he sees an image of his eye at a particular spot in the mirror and also sees the collimated light beam.

2. The method of claim 1 also comprising placing a target on the mirror which defines a particular spot where at least a portion of the reflected image is desired to be positioned.

3. The method of claim 1 also comprising placing a luminous indicator in the mirror which defines a particular spot where at least a portion of the reflected image is desired to be positioned.

4. The method of claim 1 wherein the mirror has a concave surface for magnification of the reflected image.

5. The method of claim 1 wherein the camera detects infrared light.

6. The method of claim 1 wherein the mirror is a partially-transparent mirror and the camera is positioned to receive light reflected from the eye of the subject that passes through the mirror.

7. The method of claim 1 wherein the mirror is a cold mirror and a camera is positioned to receive infrared light reflected from the eye of the subject that passes through the mirror.

8. The method of claim 1 also comprising the step of detecting a specular reflection of the light beam from at least one eye of the subject or from at least one lens of eyeglasses worn by the subject.

9. The method of claim 8 wherein the specular reflection is detected by a photodetector.

10. The method of claim 8 wherein the specular reflection is detected by the camera.

11. The method of claim 8 also comprising the step of producing an audible tone when the specular reflection is detected.

12. The method of claim 8 also comprising the step of activating a luminous indicator when the specular reflection is detected.

13. A method of positioning an eye of a subject to be photographed by a camera comprising the steps of:
  a. selecting a specific location in space within a field of view of the camera at which an eye of the subject is desired to be positioned;
  b. providing a first mirror at a fixed distance from the selected specific location in space such that the subject can see a first reflected image of his eye at a particular spot in the mirror only when his line of sight is a segment of a line that passes through the selected specific location in space;
  c. providing a second mirror at a fixed distance from the selected specific location in space such that the subject can see a second reflected image of his eye at a particular spot in this second mirror only when his line of sight is a segment of a line that passes through the selected specific location in space;
  d. instructing the subject to position his head so that he sees the first reflected image of his eye at the particular spot in the first mirror and also sees the second reflected image of his eye at the particular spot in the second mirror.

14. The method of claim 13 also comprising placing a target on at least one of the mirrors which defines the particular spot on the at least one mirror where at least a portion of one of the reflected images is desired to be positioned.

15. The method of claim 13 also comprising placing a luminous indicator in at least one of the mirrors which defines the particular spot where at least a portion of one of the reflected images is desired to be positioned.

16. The method of claim 13 wherein at least one of the mirrors has a concave surface for magnification of one of the reflected images.

17. The method of claim 13 wherein the camera detects infrared light.

18. The method of claim 17 wherein at least one of the mirrors is a cold mirror and the camera is positioned to receive infrared light reflected from the eye of the subject that passes through the cold mirror.

19. The method of claim 13 wherein at least one of the mirrors is a partially-transparent mirror and the camera is positioned to receive light reflected from the eye of the subject that passes through the at least one of the mirrors.

20. The method of claim 13 also comprising the step of detecting a specular reflection of the light beam from at least one eye of the subject or from at least one lens of eyeglasses worn by the subject.

21. The method of claim 20 wherein the specular reflection is detected by a photodetector.

22. The method of claim 20 wherein the specular reflection is detected by the camera.

23. The method of claim 20 also comprising the step of producing an audible tone when the specular reflection is detected.

24. The method of claim 20 also comprising the step of activating a luminous indicator when the specular reflection is detected.

25. A method of aiming at and focusing on an eye of a subject to be photographed by a camera having a manual focus mechanism comprising the steps of:
  a. providing a mirror such that the subject can see a reflected image of his eye at a particular spot in the mirror only when his line of sight is in the field of view of the camera;
  b. directing a collimated light beam in synchronization with the manual focus mechanism of the camera such that the eye of the subject can see the beam only when the eye is at a distance of clear focus on the line of sight established in step a; and
  d. instructing the subject to position his head so that he sees the reflected image of his eye at the particular spot in the mirror and then manually adjust the focus of the camera until he sees the collimated light beam.

26. The method of claim 25 also comprising placing a target on the mirror which defines a particular spot where at least a portion of the reflected image is desired to be positioned.

27. The method of claim 25 also comprising placing a luminous indicator in the mirror which defines the particular spot where at least a portion of a reflected image is desired to be positioned.

28. The method of claim 25 wherein the mirror has a concave surface for magnification of the reflected image.

29. The method of claim 25 wherein the camera detects infrared light.

30. The method of claim 29 wherein the mirror is a cold mirror and the camera is positioned to receive infrared light reflected from the eye of the subject that passes through the mirror.

31. The method of claim 25 wherein the mirror is a partially-transparent mirror and the camera is positioned to receive light reflected from the eye of the subject that passes through the mirror.

32. The method of claim 25 also comprising the step of detecting a specular reflection of the light beam from at least one eye of the subject or from at least one lens of eyeglasses worn by the subject.

33. The method of claim 32 wherein the specular reflection is detected by a photodetector.

34. The method of claim 32 wherein the specular reflection is detected by the camera.

35. The method of claim 32 also comprising the step of producing an audible tone when the specular reflection is detected.

36. The method of claim 32 also comprising the step of activating a luminous indicator when the specular reflection is detected.

37. A method of positioning an eye of a subject to be photographed by a camera comprising the steps of:
   a. selecting a specific location in space within a field of view of the camera at which an eye of the subject is desired to be positioned;
   b. providing a mirror at a fixed distance from the selected specific location in space such that the subject can see a reflected image of his eye at a particular spot in the mirror only when his line of sight is a segment of a line that passes through the selected specific location in space;
   c. directing a light sheet in a manner so that the light sheet passes through the selected specific location in space; and
   d. instructing the subject to position his head so that he sees the reflected image of his eye at the particular spot in the mirror and also sees the light sheet.

38. The method of claim 37 also comprising placing a target on the mirror which defines the particular spot where at least a portion of a reflected image is desired to be positioned.

39. The method of claim 37 also comprising placing a luminous indicator in the mirror which defines a particular spot where at least a portion of a reflected image is desired to be positioned.

40. The method of claim 37 wherein the mirror has a concave surface for magnification of a reflected image.

41. The method of claim 37 wherein the camera detects infrared light.

42. The method of claim 41 wherein the mirror is a cold mirror and the camera is positioned to receive infrared light reflected from the eye of the subject that passes through the mirror.

43. The method of claim 37 wherein the mirror is a partially-transparent mirror and the camera is positioned to receive light reflected from the eye of the subject that passes through the mirror.

44. The method of claim 37 also comprising the step of detecting a specular reflection of the light sheet from at least one eye of the subject or from at least one lens of eyeglasses worn by the subject.

45. The method of claim 44 wherein the specular reflection is detected by a photodetector.

46. The method of claim 44 wherein the specular reflection is detected by the camera.

47. The method of claim 44 also comprising the step of producing an audible tone when the specular reflection is detected.

48. The method of claim 44 also comprising the step of activating a luminous indicator when the specular reflection is detected.

49. A system for taking an image of a subject comprised of:
   a. a mirror positioned a fixed distance from a selected specific point in space to reflect light from a subject positioned at the selected specific point in space back to that selected specific point in space;
   b. a collimated light source positioned to direct a light beam through the selected specific point in space in a manner so that an eye positioned at the selected specific point in space can see the light beam while the subject can see a reflected image of his eye at a particular spot in the mirror when his line of sight is a segment of a line that passes from the mirror through the specific point in space; and
   c. a camera positioned so that the selected specific point in space is in the field of view of the camera.

50. The system of claim 49 also comprising a pedestal on which at least one of the camera, the mirror and the light source is mounted.

51. The system of claim 49 also comprising a secondary mirror positioned between the selected point and the mirror so that light reflected from a subject at the selected point will pass through the secondary mirror.

52. The system of claim 51 wherein the secondary mirror is a cold mirror.

53. The system of claim 51 wherein the secondary mirror is a hot mirror.

54. The system of claim 49 also comprising a target inscribed on the mirror which defines a particular spot where at least a portion of the reflected image is desired to be positioned.

55. The system of claim 49 also comprising a photodetector positioned to detect a specular reflection of the light beam from at least one eye of the subject or from a lens of eyeglasses worn by the subject.

56. The system of claim 55 also comprising a tone generator connected to the photodetector.

57. The system of claim 49 wherein the light source produces and the camera detects infrared light.

58. The system of claim 49 also comprising a luminous indicator attached to the mirror.

59. The system of claim 49 wherein the camera has a focal point at the selected specific location in space.

60. The system of claim 49 wherein the camera has a focus mechanism and the light source is connected to the focus mechanism in a manner so that movement of the focus mechanism moves the light source and the light source can only be seen by the eye when the eye is at the point at which the camera is focused.

61. A system for taking an image of a subject comprised of:
   a. a mirror positioned a fixed distance from a selected specific point in space to reflect light from a subject positioned at the selected specific point in space back to that selected specific point in space;
   b. a light source which produces a sheet of light positioned to direct the sheet of light through the selected specific point in space in a manner so that an eye positioned at the selected specific point in space can see the light while the subject can see a reflected image of his eye at a particular spot in the mirror when his line of sight is a segment of a line that passes from the mirror through the specific point in space; and
   c. a camera positioned so that the selected specific point in space is in the field of view of the camera.

62. The system of claim 61 also comprising a pedestal on which at least one of the camera, the mirror and the light source is mounted.

63. The system of claim 61 also comprising a secondary mirror positioned between the selected point and the mirror so that light reflected from a subject at the selected point will pass through the secondary mirror.

64. The system of claim 63 wherein the secondary mirror is a cold mirror.

65. The system of claim 63 wherein the secondary mirror is a hot mirror.

66. The system of claim 61 also comprising a target inscribed on the mirror which defines a particular spot where at least a portion of a reflected image is desired to be positioned.

67. The system of claim 61 also comprising a photodetector positioned to detect a specular reflection of light from at least one eye of the subject or from a lens of eyeglasses worn by the subject.

68. The system of claim 67 also comprising a tone generator connected to the photodetector.

69. The system of claim 61 wherein the light source produces and the camera detects infrared light.

70. The system of claim 61 also comprising a luminous indicator attached to the mirror.

71. The system of claim 61 wherein the camera has a focal point at the selected specific location in space.

72. The system of claim 61 wherein the camera has a focus mechanism and the light source is connected to the focus mechanism in a manner so that movement of the focus mechanism moves the light source and the light source can only be seen by the eye when the eye is at a focal point of the camera.

* * * * *